(12) United States Patent
Abe et al.

(10) Patent No.: US 10,473,622 B2
(45) Date of Patent: Nov. 12, 2019

(54) METHOD AND APPARATUS FOR FLAW INSPECTION OF FRICTION-WELD PART OF STEM IN ENGINE VALVE

(71) Applicant: NITTAN VALVE CO., LTD., Hadano-shi, Kanagawa (JP)

(72) Inventors: Yuichi Abe, Hadano (JP); Shigeru Uchida, Hadano (JP); Osamu Takahashi, Hiratsuka (JP)

(73) Assignee: Nittan Valve Co., Ltd., Hadano-shi, Kanagawa (JP)

( * ) Notice: Subject to any disclaimer, the term of this patent is extended or adjusted under 35 U.S.C. 154(b) by 44 days.

(21) Appl. No.: 15/887,986

(22) Filed: Feb. 3, 2018

(65) Prior Publication Data

US 2018/0156753 A1   Jun. 7, 2018

Related U.S. Application Data

(63) Continuation-in-part of application No. PCT/JP2015/071911, filed on Aug. 3, 2015.

(51) Int. Cl.
*G01N 27/72* (2006.01)
*G01N 27/90* (2006.01)
(Continued)

(52) U.S. Cl.
CPC ......... *G01N 27/904* (2013.01); *G01N 27/902* (2013.01); *G01N 29/043* (2013.01);
(Continued)

(58) Field of Classification Search
CPC .... G01N 27/902; G01N 27/904; G01N 29/04; G01N 29/043; G01N 29/28;
(Continued)

(56) References Cited

U.S. PATENT DOCUMENTS 2,682,802 A   7/1954   Fedorchak
2,953,233 A   9/1960   Zurheide
(Continued)

FOREIGN PATENT DOCUMENTS

DE   3636602 A1   6/1987
GB   2190889 A   12/1987
(Continued)

OTHER PUBLICATIONS

Applicant brings to the attention of the Examiner the existence of related U.S. Pat. No. 9,340,372, by the same Applicant as in the present case, which issued on May 17, 2016 from U.S. Appl. No. 14/352,450, which published as US 20150329297 A1 on Nov. 19, 2015, having entered US national stage on Apr. 17, 2014 from PCT/JP2013/052105, which was filed on Jan. 30, 2013 and which published as WO 2014118924 A1 on Aug. 7, 2014.

(Continued)

*Primary Examiner* — Thang X Le
(74) *Attorney, Agent, or Firm* — JTT Patent Services, LLC; Gerald T. Peters (57) ABSTRACT

Provided is a method for flaw inspection of a stem joint of a valve including: an internal flaw inspection step including causing a flaw detection probe to be disposed so as to face upward in water in a tank in an ultrasonic inspection chamber, holding a valve in such fashion as to cause the tip to face the flaw detection probe, and inspecting for a flaw at the interior of the stem joint; and a surface flaw inspection step including causing a flaw detection probe to be disposed horizontally in an eddy-current inspection chamber, holding a valve in such fashion as to cause the side face of a stem of the valve to be close to and facing the flaw detection probe, inspecting for a flaw on the surface of the stem joint while the flaw detection probe and the valve are made to engage in mutual rotation. The valves are transferred from a valve (Continued)

loading position to the ultrasonic inspection chamber, from the ultrasonic inspection chamber to the eddy-current inspection chamber, and from the eddy-current inspection chamber to a valve unloading position in substantially simultaneous, continuous, synchronous, and/or coordinated fashion.

5 Claims, 7 Drawing Sheets

(51) Int. Cl.
　　*G01N 29/27*　　(2006.01)
　　*G01N 29/04*　　(2006.01)
　　*G01N 29/28*　　(2006.01)
　　*G01N 29/22*　　(2006.01)
(52) U.S. Cl.
　　CPC .......... *G01N 29/223* (2013.01); *G01N 29/27* (2013.01); *G01N 29/28* (2013.01); *G01N 2291/0234* (2013.01); *G01N 2291/267* (2013.01)
(58) Field of Classification Search
　　CPC ... G01N 2291/0234; G01N 2291/0231; G01N 2291/02818; G01N 2291/02827; G01N 2291/02854; G01N 2291/02872; G01N 2291/0421; G01N 2291/267; G01N 21/85; G01N 21/9054; G01N 2021/154; F16K 49/002; F16K 37/0041; F16K 31/061
　　See application file for complete search history.

(56) References Cited

U.S. PATENT DOCUMENTS

| | | | |
|---|---|---|---|
| 3,433,346 A | 3/1969 | McCaskill | |
| 3,520,393 A | 7/1970 | Moyer | |
| 3,775,909 A | 12/1973 | Best | |
| 3,951,272 A | 4/1976 | Sankovich | |
| 4,378,493 A | 3/1983 | Dorf | |
| 4,388,989 A | 6/1983 | Edmunds | |
| 4,391,372 A | 7/1983 | Calhoun | |
| 4,884,463 A | 12/1989 | Kay | |
| 4,912,318 A | 3/1990 | Kajiura | |
| 4,917,556 A | 4/1990 | Stark | |
| 4,982,706 A * | 1/1991 | Rembold | F01L 9/025 123/90.12 |
| 5,617,945 A | 4/1997 | Takahashi | |
| 5,913,652 A | 6/1999 | Zejda | |
| 6,168,002 B1 | 1/2001 | Takahashi | |
| 6,234,321 B1 | 5/2001 | O'Connor | |
| 6,647,770 B2 * | 11/2003 | Satish | F16K 49/002 73/114.79 |
| 6,820,671 B2 | 11/2004 | Calvert | |
| 7,210,438 B2 * | 5/2007 | Canino | F01L 1/25 123/90.12 |
| 8,215,473 B2 | 7/2012 | Baccini | |
| 8,430,226 B2 | 4/2013 | Tokunaga | |
| 8,555,918 B2 * | 10/2013 | Goto | F15B 13/0402 137/552 |
| 8,967,368 B2 | 3/2015 | Cheng | |
| 9,340,372 B2 | 5/2016 | Makino et al. | |
| 9,506,381 B2 * | 11/2016 | Kubani | F01L 13/0015 |
| 2002/0195313 A1 | 12/2002 | Fujimori | |
| 2003/0034227 A1 | 2/2003 | Gerber | |
| 2003/0188953 A1 | 10/2003 | Nickey | |
| 2006/0137650 A1 * | 6/2006 | Nakamura | F02D 9/106 123/337 |
| 2007/0212260 A1 | 9/2007 | Fukuda | |
| 2009/0159152 A1 | 6/2009 | Till | |
| 2010/0192892 A1 * | 8/2010 | Huff | F01L 3/00 123/188.3 |
| 2015/0053533 A1 | 2/2015 | Osswald | |
| 2015/0329297 A1 * | 11/2015 | Makino | B65G 47/846 73/865.8 |

FOREIGN PATENT DOCUMENTS

| | | |
|---|---|---|
| JP | S52-122714 A | 10/1977 |
| JP | S63-500338 A | 2/1988 |
| JP | H01-291110 A | 11/1989 |
| JP | 1993-094761 U | 12/1993 |
| JP | H06-258295 A | 9/1994 |
| JP | H09-195033 A | 7/1997 |
| JP | 2000-006966 A | 1/2000 |
| JP | 2002-028714 A | 1/2002 |
| JP | 2003-139717 A | 5/2003 |
| JP | 2010-142770 A | 7/2010 |
| JP | 2012-007895 A | 1/2012 |
| WO | 2014-118924 A1 | 8/2014 |

OTHER PUBLICATIONS

International Search Report (ISR) dated Oct. 20, 2015, Written Opinion (WrOp) dated Oct. 20, 2015, and International Preliminary Report on Patentability (IPRP) dated Oct. 31, 2016 in PCT/JP2015/071911, which was filed on Aug. 3, 2015, which published as WO/2017/022046 on Feb. 9, 2017, and of which the present application is a bypass continuation-in-part application.

\* cited by examiner

METHOD AND APPARATUS FOR FLAW INSPECTION OF FRICTION-WELD PART OF STEM IN ENGINE VALVE

CROSS-REFERENCE TO RELATED APPLICATION, BENEFIT CLAIM, AND INCORPORATION BY REFERENCE

This application is a continuation-in-part of and claims benefit under 35 USC 120 and 365(c) to copending International Application No. PCT/JP2015/071911, entitled "Flaw Inspection Method and Device for Engine Valve Shaft Connection Part", filed 3 Aug. 2015, the content of which is incorporated herein in its entirety by reference.

FIELD OF THE INVENTION

The present invention relates to inspection for discovery of potential flaws at external surface(s) and within interior(s) of metal part(s), especially metal part(s) having long, slender portion(s) such as an engine valve.

In particular, the present invention relates to methods and apparatuses for flaw inspection of a friction-weld joint or other such stem joint of an engine valve such as may be carried out through use of an ultrasonic flaw detection probe and an eddy-current flaw detection probe.

BACKGROUND

Figure 1:
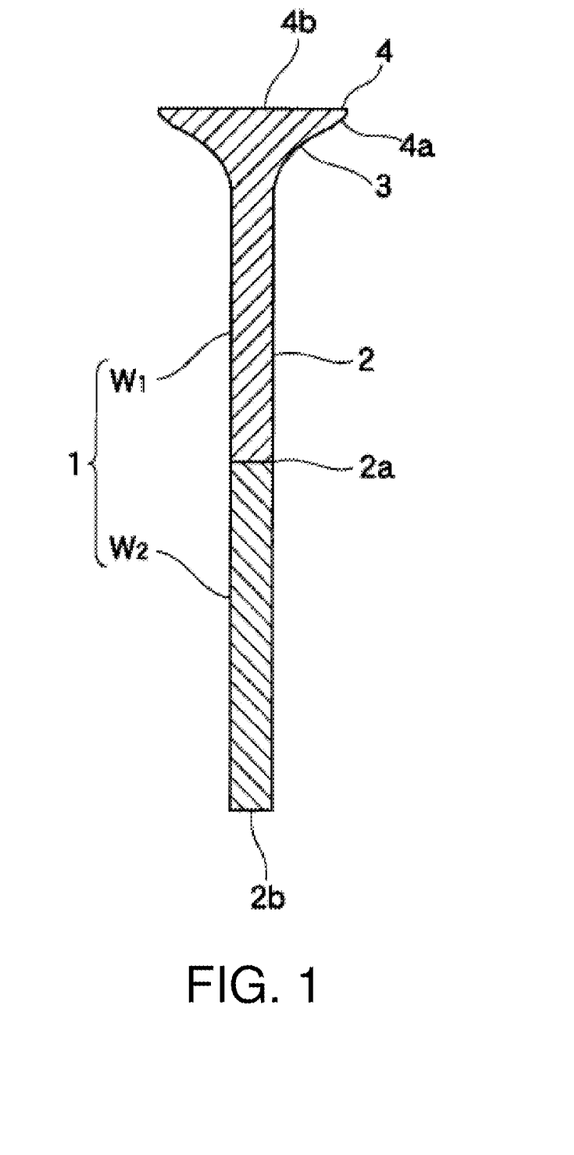
FIG. 1 is a longitudinal sectional view showing a friction-weld joint at a stem in an engine valve for a combustion engine, the valve being an example of an object to be inspected by means of a flaw inspection method according to the present invention.

Referring to FIG. 1, an engine valve 1 for an automobile might comprise a stem 2, and a valve head 4 integrally formed at one end of the stem 2. In particular, when the engine valve 1 is used as an exhaust valve, the valve head 4, because it will be exposed to combustion gas from the combustion chamber and exhaust passages, preferably has high heat resistance. In contrast, the heat resistance of the stem 2 generally need not be as high as that of the valve head 4.

This being the case, there are valves in which a valve head member made, of a metal having high heat resistance is integrally joined by means of friction welding or the like to a stem member made of a metal having lower heat resistance but excellent mechanical strength, for example. A valve made by such a process may be advantageous because it may permit achievement of both durability and cost reduction as a result of judicious selection of metals having properties respectively suitable for the valve head and the valve stem.

Although the description which follows is given in terms of the example of a valve in which a friction-weld joint or other such stem joint is employed to join a head member and a stem member of an engine valve, the present invention is not limited to engine valves but may be applied to friction-weld parts in general. Furthermore, the present invention is not limited to friction-weld joints or stem joints but may be applied to detection of flaws in general; for example, the present invention may be used to detect flaws at joints between metal parts regardless of the type of joint employed to join those parts.

One type of device that may be used for inspection of a welded joint is an apparatus including a sensor unit equipped with an eddy-current flaw detection sensor and an ultrasonic flaw detection sensor. The sensor unit might move along a welded joint, and, when the eddy-current flaw detection sensor detects a surface flaw on the joint, the sensor unit might stop moving at the position where the surface flaw is detected to inspect the interior of the joint (hereinafter referred to as "internal flaw inspection") through use of an ultrasonic flaw detection sensor.

While such an inspection apparatus can be effective for flaw inspection of a joint of a planar metal member, it is less efficiently used to perform an inspection, especially an internal flaw inspection, of an object such as an engine valve which is comparatively small, and whose stem, which may include a joint comprising a friction-weld joint or other such stem joint, has an elongated columnar shape.

In another method for internal flaw inspection of a joint, an ultrasonic flaw detection sensor is made to face an end face of a rod-like metal member having the joint in the longitudinal middle thereof in such fashion as to cause an ultrasonic wave to enter from the end face of the rod-like member. It should be noted that this method is preferably carried out with interposition of a contact medium (for example, water or oil) between the ultrasonic flaw detection sensor and the end face of the rod-like member to increase transmission efficiency of the ultrasonic wave. This method therefore tends to be troublesome, and automation of internal flaw inspection is difficult when this method is used.

Further, in another method for internal flaw inspection of a joint of a rod-like metal member, an ultrasonic flaw detection sensor might be provided in a tank filled with water as contact medium and a rod-like metal member might be held in such fashion as to cause the end face thereof to face the ultrasonic flaw detection sensor in the water (hereinafter referred to as "water immersion flaw detection method"). In such a situation, if water serving as contact medium is always interposed between the ultrasonic flaw detection sensor and the end face of the rod-like member, this may facilitate automation of internal flaw inspection.

As described above, surface flaw inspection of a stem joint may be performed through use of a surface flaw inspection apparatus equipped with an eddy-current flaw detection sensor, and internal flaw inspection of the stem joint may be performed through use of an internal flaw inspection apparatus equipped with an ultrasonic flaw detection sensor, particularly an internal flaw inspection apparatus configured to hold a valve in such a way that a tip of the stem of the valve faces the ultrasonic flaw detection sensor which is disposed in a tank filled with water serving as contact medium.

However, problems such as the following may arise in connection with flaw inspection of a stem joint of a valve when carried out as described above.

First, two independent inspection apparatuses, that is, a surface flaw inspection apparatus and an internal flaw inspection apparatus, are required, resulting in large equipment size and increasing cost accordingly.

Secondly, cycle time for the flaw inspection process to complete is long even when the two flaw inspection apparatuses are positioned adjacent each other because a valve which finishes inspection by one apparatus must be conveyed to the other apparatus and then loaded into the other apparatus.

There is therefore need for a method and apparatus for flaw inspection of a stem joint of an engine valve that would use an ultrasonic flaw detection probe and an eddy-current flaw detection probe in a manner that would permit downsizing of equipment and shortening of inspection cycle time.

In accordance with one aspect of the present invention, the two inspection apparatuses are integrated into a single unit. In some embodiments, such integration of the two inspection apparatuses makes it possible to downsize the flaw inspection equipment and to shorten the cycle time required for the flaw inspection through one or more of the following: causing an ultrasonic flaw inspection chamber and an eddy-current flaw inspection chamber to be disposed adjacent to each other in a housing; arranging three valve supports at intervals corresponding to a distance between the two inspection chambers one by one in the horizontal direction in which both inspection chambers are adjacent each other; and moving the three valve supports integrally in the horizontal direction and in the vertical direction, so that a new valve at a location outside the inspection apparatus, a valve which has completed inspection in the first inspection chamber, and a valve which has completed inspection in the second inspection chamber can be transferred, respectively, to the first inspection chamber, the second inspection chamber, and to a location outside the apparatus.

The present inventors have constructed prototypes of flaw inspection apparatuses embodying the foregoing features and have verified the advantageous effects thereof.

SUMMARY OF INVENTION

The present invention relates to methods and apparatuses for flaw inspection of a friction-weld joint or other such stem joint of an engine valve such as may be carried out through use of an ultrasonic flaw detection probe and an eddy-current flaw detection probe. Although the description which follows is given in terms of the example of a valve in which a friction-weld joint or other such stem joint is employed to join a head member and a stem member of an engine valve, the present invention is not limited to engine valves but may be applied to friction-weld joints and other such stem joints in general. Furthermore, the present invention is not limited to stem joints but may be applied to detection of flaws in general; for example, the present invention may be used to detect flaws at joints between metal parts regardless of the type of joint employed to join those parts.

To address one or more of the needs described above, one embodiment of the present invention is a method for flaw inspection of the interior and surface of a stem joint of an engine valve through use of an ultrasonic flaw detection probe and an eddy-current flaw detection probe, the method including an internal flaw inspection step including, in the ultrasonic inspection chamber in a housing, causing the ultrasonic flaw detection probe to be disposed so as to face upward in water in a tank, holding a valve in such a way that a tip of a stem of the valve faces the ultrasonic flaw detection probe in the water, and inspecting the interior of the stem joint with the ultrasonic flaw detection probe, and a surface flaw inspection step including, in an eddy-current inspection chamber adjacent to the ultrasonic inspection chamber in the housing, causing the eddy-current flaw detection probe to be disposed horizontally, holding a valve in such a way that a lower side face of a stem of the valve including a stem joint is close to and faces the eddy-current flaw detection probe, and inspecting for a flaw on a surface of the stem joint with the eddy-current flaw detection probe while causing the eddy-current flaw detection probe to revolve about, and relative to, the outer periphery of the stem of the valve. A valve transfer mechanism which advances and recedes in a horizontal direction and in which both inspection chambers are adjacent to each other may transfer a valve at a predetermined loading position to the ultrasonic inspection chamber, a valve after internal flaw inspection in the ultrasonic inspection chamber to the eddy-current inspection chamber, and a valve after the surface flaw inspection in the eddy-current inspection chamber to a predetermined unloading position in substantially simultaneous, continuous, synchronous, and/or coordinated fashion while keeping each valve with each respective stem directed downward.

Another embodiment is an apparatus for flaw inspection of the interior and surface of a stem joint of an engine valve through use of an ultrasonic flaw detection probe and an eddy-current flaw detection probe including a housing, an ultrasonic inspection chamber provided in the housing and including the ultrasonic flaw detection probe, and an eddy-current inspection chamber provided in the housing adjacent to the ultrasonic inspection chamber in a horizontal direction the ultrasonic inspection chamber including the ultrasonic flaw detection probe, a tank in which the ultrasonic flaw detection probe is disposed so as to face upward in water, and a first valve holding mechanism holding a valve at a predetermined position in which a tip of the stem of the valve faces the ultrasonic flaw detection probe, the eddy-current inspection chamber including the eddy-current flaw detection probe which is disposed horizontally, a second valve holding mechanism holding a valve at a predetermined position at which a lower side face of a stem of the valve including a stem joint is made to be close to and facing the eddy-current flaw detection probe, and a rotation mechanism that causes the eddy-current flaw detection probe to revolve about, and relative to, the outer periphery of the stem of the valve, the housing including a valve transfer mechanism having three valve supports positioned at intervals of a distance between the first and the second valve holding mechanisms along the horizontal direction in which the ultrasonic inspection chamber and the eddy-current inspection chamber are adjacent and supporting the valves with the stems of the valves facing downward, the valve transfer mechanism transferring a valve from a predetermined loading position to the first valve holding mechanism, a valve which has completed internal flaw inspection and is held by the first valve holding mechanism to the second valve holding mechanism, and a valve which has completed surface flaw inspection and is held by the second valve holding mechanism to a predetermined unloading position, in substantially simultaneous, continuous, synchronous, and/or coordinated fashion, by virtue of the fact that the valve supports move integrally in the horizontal direction and vertical direction, while keeping each valve with each respective stem directed downward, and a control unit controlling drive of the valve transfer mechanism, the first and the second valve holding mechanisms, the ultrasonic flaw detection probe, the eddy-current flaw detection probe, and the rotation mechanism.

In accordance with one or more embodiments of the present invention, driving of the valve transfer mechanism, that is, integral movement of the valve supports in the horizontal direction and the vertical direction (advancing/receding motion and ascending/descending motion), may permit transfer of a valve from a predetermined loading position to the ultrasonic inspection chamber, a valve which has completed internal flaw inspection in the ultrasonic inspection chamber to the eddy-current inspection chamber, and a valve which has completed surface flaw inspection at the eddy-current inspection chamber to the predetermined unloading position, in substantially simultaneous, continuous, synchronous, and/or coordinated fashion.

In a preferred embodiment, the valve supports support the corresponding valves, the first of which held at the predetermined loading position, the second of which held in the first valve holding mechanism, the third of which held in the second valve holding mechanism to integrally move in a forward direction and an ascending/descending direction to respectively transfer the valves to the first valve holding mechanism, to the second valve holding mechanism, and to the predetermined unloading position. Then, by the time when the valve supports emptied as a result of transfer of the valves move integrally in a backward direction and in the ascending/descending direction to return to their initial positions, flaw inspection of the valve transferred to the first valve holding mechanism through use of the ultrasonic flaw detection probe is finished in the ultrasonic inspection chamber and flaw inspection of the valve transferred to the second valve holding mechanism through use of the eddy-current flaw detection probe are finished in the eddy-current inspection chamber. Accordingly, by repeating the forward/backward motion and the ascending/descending motion that the valve supports integrally move in the horizontal direction and the vertical direction three times, a valve at the predetermined loading position is transferred to the ultrasonic inspection chamber to have an internal flaw inspection of the stem joint. Then, the valve is transferred to the eddy-current inspection chamber to have a surface flaw inspection of the stem joint. Thereafter, the valve is transferred to the predetermined unloading position.

In contradistinction to an embodiment in which two independent inspection apparatuses (an eddy-current flaw inspection apparatus and an ultrasonic flaw inspection apparatus) are required for flaw inspection of a stem joint of a valve, in a preferred embodiment of the present invention it is possible to perform the flaw inspection through use of only one inspection apparatus including an ultrasonic inspection chamber equipped with an ultrasonic flaw detection probe and an eddy-current inspection chamber equipped with an eddy-current flaw detection probe, the ultrasonic inspection chamber and the eddy-current inspection chamber integrated adjacent to each other in a housing.

In contradistinction to an embodiment in which two operations, that is, taking out (transferring) a valve which has completed inspection in one inspection apparatus to a location outside the apparatus and introducing (transferring) the valve to the other inspection apparatus are separately performed, in a preferred embodiment of the present invention the two operations can be performed as a series of operations of transferring the valve from the ultrasonic inspection chamber to the eddy-current inspection chamber, which leads to shortening of the cycle time of the flaw inspection process.

With respect to the procedure of the flaw inspection of the stem joint at the valve, whereas performing a surface flaw inspection step firstly and then an internal flaw inspection step may result in a situation in which water adhering to the valve after the internal flaw inspection step causes a valve conveyance path extending from the flaw inspection process to become wet. Where this is the case, this might be addressed by providing the flaw inspection process with a water removing means such as a dryer or a fan.

However, in accordance with a preferred embodiment of the present invention, after the internal flaw inspection step is performed in a manner in which the stem of the valve is immersed in water in the ultrasonic inspection chamber, the surface flaw inspection step is performed in the eddy-current inspection chamber. In addition, the valve transferred from the ultrasonic inspection chamber to the eddy-current inspection chamber and the valve transferred from the eddy-current inspection chamber to the predetermined unloading position are oriented such that the stems are directed downward. Accordingly, the water adhering to the stem of the valve falls downward from the stem end during the transfer of the valve. As a result, very little water remains on the stem joint of the valve transferred to the eddy-current inspection chamber. And note that even if some small amount of water remains on the stem including the stem joint, this will not adversely affect the surface flaw inspection using the eddy-current flaw detection probe.

Further, even where water remains on the valve after the surface flaw inspection is finished in the eddy-current inspection chamber, such water would, in such an embodiment, be made to definitively flow down and off the stem side of the valve during conveyance of the valve to the following process. Accordingly, in such an embodiment, there is little or no possibility that water will continue to adhere to the valve when it is conveyed to the subsequent operation in the flaw inspection process.

In accordance with another embodiment of the present invention, the valve transfer mechanism may include a slide frame capable of advancing and receding in the horizontal direction in which the ultrasonic inspection chamber and the eddy-current inspection chamber are adjacent to each other and the valve supports which are mounted so as to be capable of ascending/descending in the vertical direction with respect to the slide frame.

By causing the valve supports to be configured in such a manner as to both ascend and descend in the vertical direction with respect to the slide frame capable of advancing and receding in the horizontal direction, the structure and the driving control of the valve transfer mechanism may become accordingly complicated. However, there are advantages as described below.

That is, valves to be inspected may include valves having different specifications such as different values for the diameter of the valve head or different values for total length. Accordingly, valve transfer positions in the valve transfer mechanism including the predetermined valve loading position and the predetermined valve unloading position may be different in the vertical direction. However, since the valve supports can separately ascend and descend with respect to the slide frame, it is possible to accommodate such differences by adjusting the amount by which valve supports ascend and/or descend in the vertical direction in accordance with the specifications of the valve or height of the valve transfer positions without any need to change valve transfer positions.

In accordance with another embodiment of the present invention, the valve transfer mechanism may include a slide frame capable of advancing and receding in a horizontal direction in which the ultrasonic inspection chamber and the eddy-current inspection chamber are adjacent to each other and capable of ascending and descending in the vertical direction, and a valve support which is integrated with the slide frame.

Where this the case, because the slide frame is configured in such a manner as to be capable of advancing and receding in the horizontal direction and capable of ascending and descending in the vertical direction, the valve support can move integrally in the horizontal direction and the vertical direction even if the valve support is not configured in such a manner as to be capable of ascending and descending in the vertical direction with respect to the slide frame as in the third aspect. Accordingly, the configuration of the valve transfer mechanism can be simplified.

Note that in embodiments in which the valve supports do not ascend and descend in the vertical direction with respect to the slide frame, the driving control of the valve transfer mechanism can be simplified.

BENEFIT OF INVENTION

Some embodiments of the present invention make it possible to perform an internal and surface flaw inspection of a stem joint of a valve through use of a single flaw inspection apparatus so that flaw inspection equipment can be downsized and simplified.

Further, transfer of a valve from the predetermined loading position to the ultrasonic inspection chamber, transfer of a valve from the ultrasonic inspection chamber to the eddy-current inspection chamber, and transfer of a valve from the eddy-current inspection chamber to the predetermined unloading position may be performed in substantially simultaneous, continuous, synchronous, and/or coordinated fashion. In particular, in contradistinction to methods in which transfer of the valve from the ultrasonic inspection chamber and transfer of the valve into the eddy-current inspection chamber are performed separately, i.e., in space or in time, in a preferred embodiment of the present invention transfer of the valve from the ultrasonic inspection chamber and transfer of the valve into the eddy-current inspection chamber are performed substantially simultaneously, consecutively, or in a substantially continuous series of operations of transfer of the valve from the ultrasonic inspection chamber to the eddy-current inspection chamber.

For example, in some embodiments, valves may be processed continuously with efficient sharing of space within the device, such that as a downstream valve finishes processing in a first chamber and leaves the first chamber to enter a second chamber, an upstream valve need not wait for the downstream valve to exit device but can enter the second chamber as soon as the second chamber has been vacated by the downstream valve.

Furthermore, in some embodiments, valves may be processed substantially synchronously and/or in substantially coordinated fashion. In some embodiments, valves may be processed in substantially linked, ganged, and/or interlocking fashion. In some embodiments, multiple valves may be processed in parallel rather than serial fashion.

Such shared and/or efficient use of space and/or time may permit the cycle time for the internal flaw inspection and surface flaw inspection of the stem joint of the valve to be shortened significantly as compared with other methods.

Moreover, in a present embodiment, since a valve on which water adheres is not conveyed to the subsequent process via the valve conveyance path, there will in such an embodiment be little or no possibility that the valve conveyance path becomes wet, or that the water adhering to the valve interferes with processing during the subsequent process, eliminating the need to provide a water removing means such as a dryer or blower in the flaw inspection process.

Some embodiments of the present invention make it possible to perform flaw inspection of various valves having different specifications without changing the structure of the apparatus by adjusting amounts by which valve support(s) ascend and descend in the vertical direction in accordance with the specification of the valve. Accordingly, in such embodiments, a flaw inspection apparatus which is excellent in versatility can be provided.

Furthermore, because in some embodiments the structure of the valve transfer mechanism is made simple, the driving control of the valve transfer mechanism is simplified accordingly, thereby reducing a cost of the flaw inspection apparatus.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Embodiments of the present invention will be described on the basis of examples. Although the description which follows is given in terms of the example of a valve in which a friction-weld joint or other such stem joint is employed to join a head member and a stem member of a valve for use in an engine, the present invention is not limited to engine valves but may be applied to friction-weld joints and other such stem joints in general. Furthermore, the present invention is not limited to stem joints but may be applied to detection of flaws in general; for example, the present invention may be used to detect flaws at joints between metal parts regardless of the type of joint employed to join those parts.

FIG. 1 illustrates an example of a friction-weld joint at a stem in an engine valve for a combustion engine. A poppet valve 1 includes a stem 2 extending in straight fashion, and a valve head 4 formed as to be integral with the stem 2 at one end of the stem 2 via a fillet portion 3 of round shape which is such that the outer diameter thereof gradually increases as one proceeds toward valve face 4b. The head 4 has a tapered valve seat 4a at an outer periphery thereof. Note that reference numeral 4b denotes what will be referred to as the face of valve 1, and reference numeral 2b denotes what will be referred to as the tip of valve 1.

In detail, the poppet valve 1 includes a portion W1 at the head 4 side thereof serving as intermediate member which is made of a metal having excellent heat resistance (for example, SUH35), a portion W2 at the tip side thereof serving as tip member which is made of a metal having high mechanical strength (for example, SUH11), and a joint 2a by means of which the head portion W1 and the tip portion W2 are integrally joined with each other at their respective ends by friction welding, for example. Such a friction-weld joint or other such stem joint 2a between the head portion (intermediate member) W1 and the tip portion (tip member) W2 can be seen in the middle of the stem 2 in the drawing at FIG. 1. Note, however, that in a real valve it may be difficult or impossible to detect the stem joint with the naked eye.

Next, an apparatus for flaw inspection of a stem joint of a valve according to a first example of the present invention will be described with reference to FIGS. 2 to 5.

In FIGS. 2 to 5, an ultrasonic inspection chamber 20 equipped with an ultrasonic flaw detection probe 22 (see FIG. 4) and an eddy-current inspection chamber 30 equipped with an eddy-current flaw detection probe 32 (see FIG. 5) are provided adjacent to each other in a horizontal direction (i.e., the horizontal direction as viewed at FIGS. 2 and 3) within a housing 12 of the flaw inspection apparatus 10.

Figure 4:
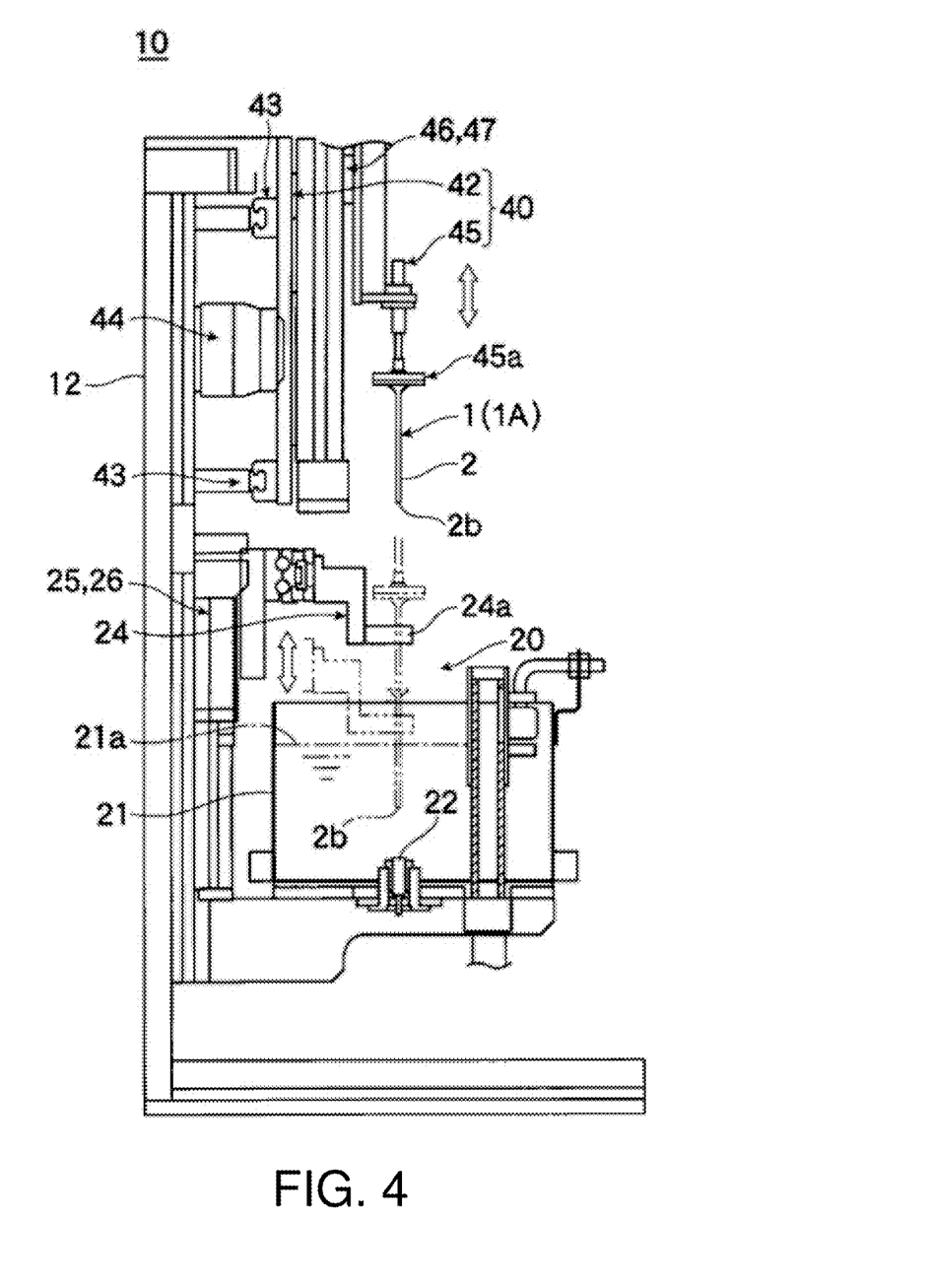
FIG. 4 is a longitudinal sectional view (taken along IV-IV shown in FIGS. 2 and 3) of the ultrasonic inspection chamber in the flaw inspection apparatus.

As illustrated in FIG. 4, a tank 21 containing water 21a is disposed in the ultrasonic inspection chamber 20. The ultrasonic flaw detection probe 22 is disposed in upwardly directed fashion at the bottom of the tank 21. Provided above the tank 21 is a first chuck 24, which serves as a first valve holding mechanism, holding a valve 1 such that the first chuck 24 ascends and descends in the vertical direction in such fashion as to be capable of being positioned at a predetermined position at which the tip 2b of the stem 2 is made to face the ultrasonic flaw detection probe 22 in the water.

The first chuck 24 has a pair of claws 24a (see FIGS. 3 and 4) openable in the horizontal direction by means of an air cylinder (not shown). The first chuck 24 can ascend and descend in the vertical direction with respect to the housing 12, as illustrated by an arrow in FIG. 4, by means of a servo motor 25 and a drive mechanism 26 including a linear guide and a ball screw. The servo motor 25 and the drive mechanism 26 are interposed between the first chuck 24 and the housing 12.

For this reason, in the ultrasonic inspection chamber 20, as illustrated in FIG. 4, a valve 1 which is transferred from a predetermined loading position P1 (see FIG. 2) by a valve transfer mechanism 40, described below, with the stem 2 directed downward, is clamped by the first chuck 24 and made to descend to a predetermined position at which the tip 2b of the stem 2 is made to face the ultrasonic flaw detection probe 22 in the water so as to permit it to be subjected to an internal flaw inspection of the stem joint 2a by the ultrasonic flaw detection probe 22. The inspection by the ultrasonic flaw detection probe 22 is completed nearly instantaneously, and following inspection the valve 1 is made to ascend to its initial position by the first chuck 24 so that it can be transferred to the neighboring eddy-current inspection chamber 30 by the valve transfer mechanism 40.

Figure 5:
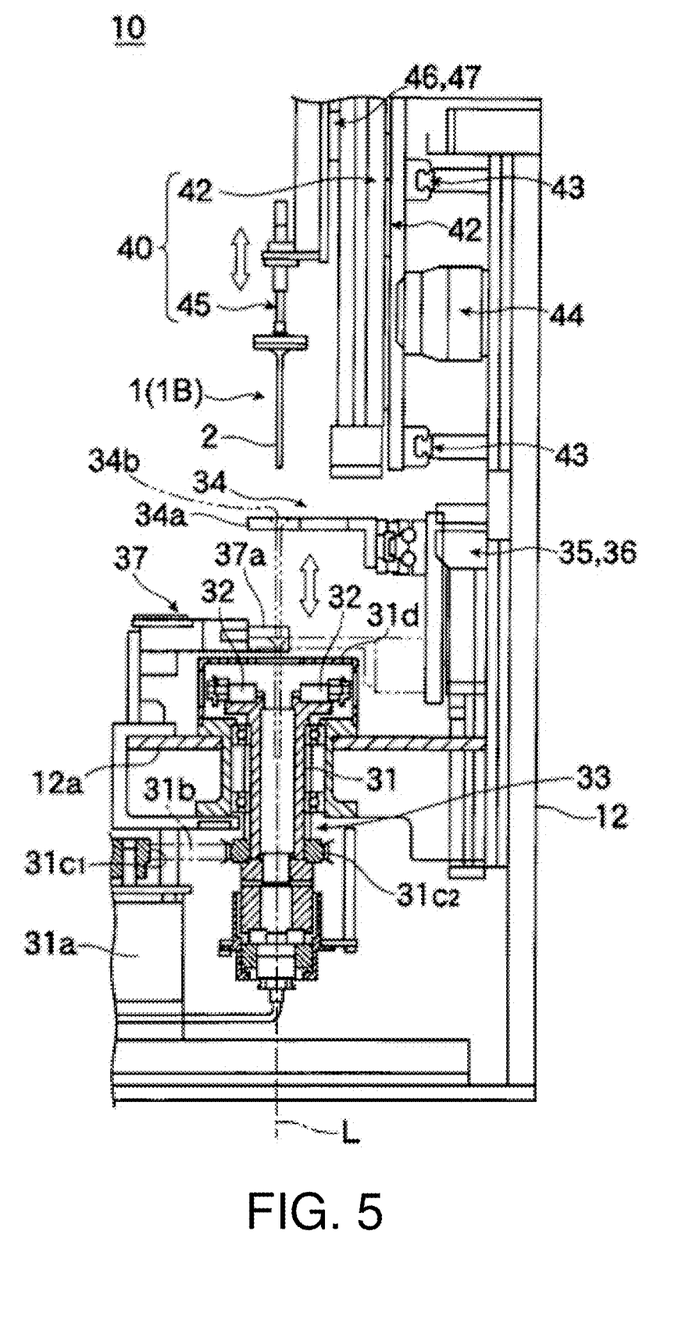
FIG. 5 is a longitudinal sectional view (taken along V-V shown in FIGS. 2 and 3) of the eddy-current inspection chamber in the flaw inspection apparatus.

On the other hand, in the eddy-current inspection chamber 30, as illustrated in FIG. 5, the eddy-current flaw detection probes 32 are arranged so as to be mutually opposed in the horizontal direction. Provided above the probes 32 is a second chuck 34 which serves as a second valve-holding mechanism, clamping a valve 1 transferred thereto from the ultrasonic inspection chamber 20 by the valve transfer mechanism 40 to hold the valve 1 at a predetermined position at which a side face of the stem 2 including the stem joint 2a is made to be close to and face the eddy-current flaw detection probe 32. That is, the second chuck 34, as with the first chuck 24 in the ultrasonic inspection chamber 20, has a pair of claws 34a (see FIGS. 3 and 5) openable in the horizontal direction by means of an air cylinder (not shown). The second chuck 34 can ascend and descend in the vertical direction with respect to the housing 12, as illustrated by arrows in FIG. 5, by means of a servo motor 35 and a drive mechanism 36 including a linear guide and a ball screw. The servo motor 35 and the drive mechanism 36 are interposed between the second chuck 34 and the housing 12.

The pair of claws 34a constituting the second chuck 34 is configured in such a manner as to cooperatively form a valve head receiving face having an arcuate cross-section which is continuous in the circumferential direction when closed, to support the valve head 4. The valve 1 ascends and descends with the valve head 4 supported by (the pair of claws 34a of) the second chuck 34

Further, as illustrated in FIG. 5, a cylindrical body 31 elongated in the vertical direction is rotatably supported by a horizontal base plate 12a fixed to the housing 12. On the inner side of the upper end portion increasing diameter of the cylindrical body 31, the flaw detection probes 32 is provided opposite to each other interposing the rotation central axis L of the cylindrical body 31. The flaw detection probes 32 and the cylindrical body 31 are configured in such a manner as to rotate integrally. Reference numerals 31a and 31b respectively denote a drive motor and a belt; and reference numerals 31c1 and 31c2 respectively denote a drive pulley and a driven pulley. Reference numeral 31d denotes a cylindrical probe cover fixed to the horizontal base plate 12a and covering the flaw detection probe 32.

That is, the drive motor 31a, the drive pulley 31c1, the belt 31b, the driven pulley 31c2 and the cylindrical body 31 constitutes a rotation mechanism 33 which rotates the eddy-current flaw detection probe 32 along an outer periphery of (the stem joint 2a of) the stem 2.

Moreover, provided in the vicinity of region directly above the probe cover 31d is an aligning guide 37 capable of guiding the stem 2 of the valve 1 held by the second chuck 34 to the cylindrical body 31. The aligning guide 37 has a pair of claws 37a openable by 180° in the horizontal direction by means of an air cylinder (not shown). When the pair of claws 37a closing, abutting parts of the pair of claws 37a cooperatively form a tapered guide hole to securely guide the stem 2 of the valve 1 descending integrally with the second chuck 34 which being supported by the second chuck 34 along the rotational central axis L of the cylindrical body 31.

As the aligning guide 37 opens in synchronism with descent of the second chuck 34, the second chuck 34 can descend to a predetermined position approaching the cover 31d without interfering the aligning guide 37. That is, as it is possible to increase an amount by which the stem 2 is inserted into the cylindrical body 31 equipped with the eddy-current flaw detection probes 32, the eddy-current flaw inspection of a valve 1 having a specification that the stem joint 2a is near the valve head 4 in the valve 1, that is, the stem joint 2a is located at a position close to the fillet portion 3, can be performed.

For this reason, in the eddy-current inspection chamber 30, as illustrated in FIG. 5, the valve 1 which is transferred from the ultrasonic inspection chamber 20 by the valve transfer mechanism 40, described below, with the valve stem 2 directed downward, is supported by the second chuck 34 and made to descend with the side face of the stem 2 including the stem joint 2a close to and facing the eddy-current flaw detection probe 32, so that the eddy-current flaw detection probes 32 perform a surface flaw inspection of the entire periphery of the stem joint 2a. As with the inspection carried out by the ultrasonic flaw detection probe 22, the inspection carried out by the eddy-current flaw detection probes 32 is completed nearly instantaneously, and following inspection the valve 1 is made to ascend to its initial position by the second chuck 34 so that it can be transferred to a predetermined unloading position P2 by the valve transfer mechanism 40 (see FIG. 2).

Figure 2:
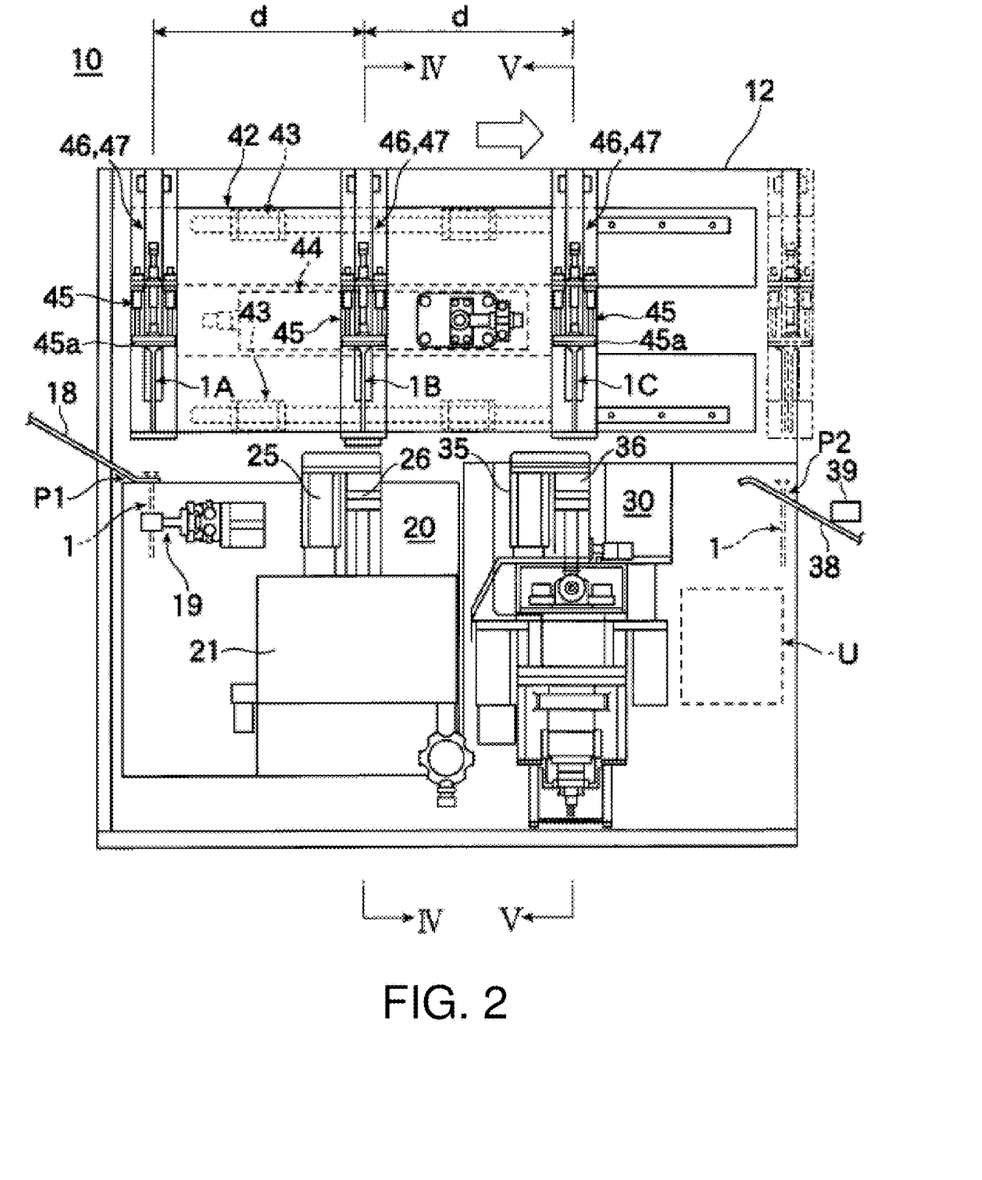
FIG. 2 is a front view of a flaw inspection apparatus according to a first example of the present invention.
Figure 3:
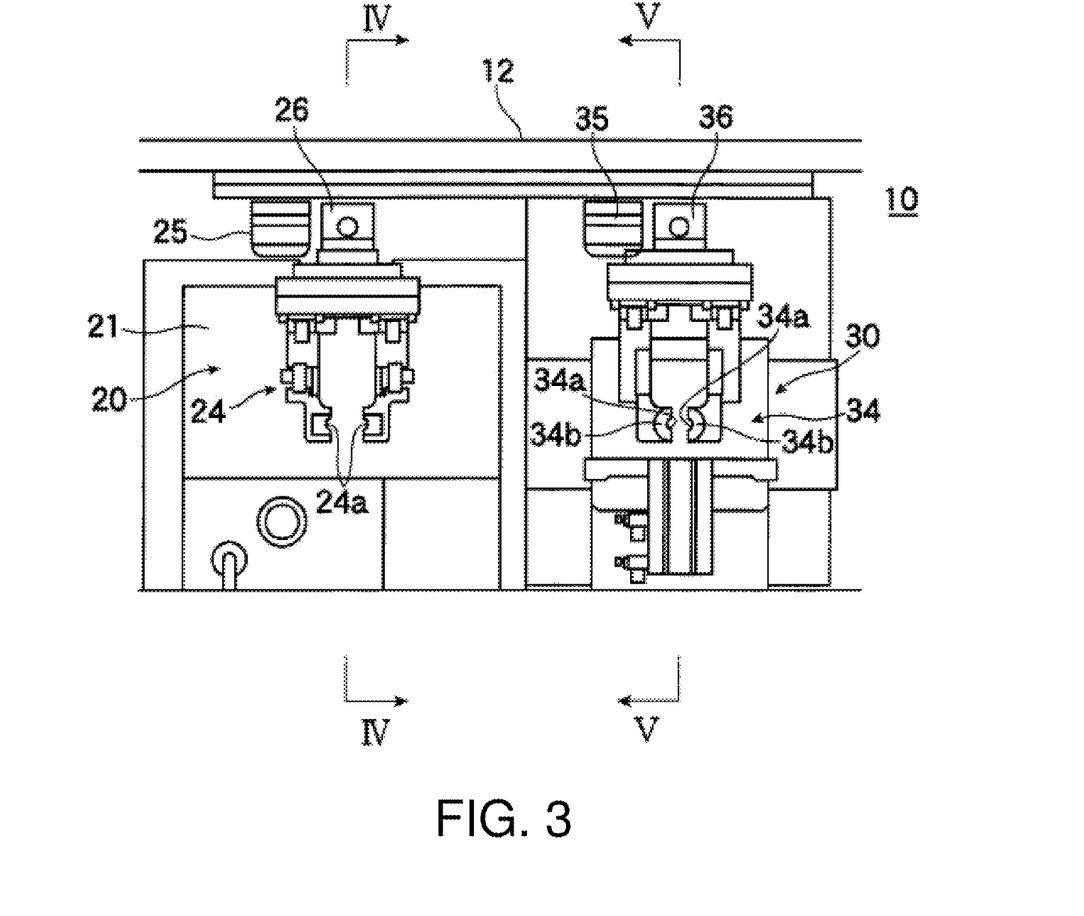
FIG. 3 is a plan view of first and second valve holding mechanisms respectively provided in ultrasonic inspection and eddy-current inspection chambers in the flaw inspection apparatus.

It should be noted that the first chuck 24 provided in the ultrasonic inspection chamber 20 and the second chuck 34 provided in the eddy-current inspection chamber 30 are omitted in FIG. 2.

Referring now to FIG. 2, the valve transfer mechanism 40 will be described. The valve transfer mechanism 40 is arranged at the back side of the ultrasonic inspection chamber 20 and the eddy-current inspection chamber 30, which are adjacent to each other side-by-side, and the valve transfer mechanism 40 transfers a valve 1 from the predetermined valve loading position P1 to the ultrasonic inspection chamber 20, a valve 1 which has completed inspection in the ultrasonic inspection chamber 20 to the eddy-current inspection chamber 30, and a valve 1 which has completed inspection in the eddy-current inspection chamber to the predetermined valve unloading position P2, in substantially simultaneous, continuous, synchronous, and/or coordinated fashion. The direction in which the valve transfer mechanism 40 transfers the valve 1 is from left to right as viewed in FIG. 2, as illustrated by an arrow in same drawing.

The valve transfer mechanism 40 includes a slide frame 42 which advances and recedes in the horizontal direction at a back side of the ultrasonic inspection chamber 20 and the eddy-current inspection chamber 30. The slide frame 42 is formed in a rectangular shape in front view having predetermined lengths in the horizontal and vertical direction. The slide frame 42 can advance and recede in the horizontal direction with respect to the housing 12 by means of a linear guide 43 extending in the horizontal direction and a drive mechanism 44 including a servo motor and a ball screw. The linear guide 43 and the drive mechanism 44 are interposed between the valve transfer mechanism 40 and the housing 12.

On a side face of the slide frame 42 facing the ultrasonic inspection chamber 20 and the eddy-current inspection chamber 30, three suction-pad jigs 45 each serving as a valve support to support a valve 1 with a stem 2 directed downward are provided at predetermined intervals d corresponding to a distance between the first chuck 24 and the second chuck 34 in the horizontal direction.

The suction-pad jig 45 has a suction pad 45a sucking the valve face 4b with negative pressure. The suction-pad jig 45 can ascend and descend in the vertical direction with respect to the slide frame 42 by means of a linear guide 46 and a drive mechanism 47 including a servo motor and a ball screw. The linear guide 46 and the drive mechanism 47 are interposed between the suction-pad jigs 45 and the slide frame 42.

That is, the slide frame 42 which advances and recedes in the horizontal direction and the three suction-pad jigs 45 constitute the valve transfer mechanism 40 which transfer a valve 1 which has been loaded at the predetermined loading position P1 to the first chuck 24 in the ultrasonic inspection chamber 20, a valve 1 which is held by the first chuck 24 following internal flaw inspection to the second chuck 34 in the eddy-current inspection chamber 30, and a valve 1 which is held by the second chuck 34 following surface flaw inspection to the predetermined valve unloading position P2, in substantially simultaneous, continuous, synchronous, and/or coordinated fashion, while keeping the valves 1 with the respective stems 2 directed downward.

As shown in FIG. 2, at the valve loading position P1, a valve 1 loaded via a valve loading slider 18 is suspended and held with the face 4a facing upward (the stem 2 directed downward). Just below the valve loading position P1, provided is a chuck 19 to clamp the stem 2 in synchronism with the descending of the suction-pad jig 45 in the valve transfer mechanism 40 to hold the valve 1 in such fashion as to cause the face 4a to face the suction pad 45a which descends from thereabove. Then, at the same time of the suction-pad jig 45 descending to suck the face 4a, the chuck 19 releases clamping of the stem 2.

On the other hand, at the valve unloading position P2, a valve unloading slider 38 is provided. A valve 1 transferred to the valve unloading position P2 by the valve transfer mechanism 40 is made to slide along the slider 38 under its own weight.

Further, provided at the back side of the housing 12 is a control unit U (see FIG. 2) to control driving of the chuck 19 at the valve loading position P1, the valve transfer mechanism 40 (the slide frame 42, the suction-pad jigs 45), the first chuck 24 and ultrasonic flaw detection probe 22 in the ultrasonic inspection chamber 20, the second chuck 34, aligning guide 37, eddy-current flaw detection probe 32 and rotating mechanism 33 in the eddy-current inspection chamber 30.

Moreover, the control unit U compares the flaw inspection data acquired via the ultrasonic flaw detection probe 22 and eddy-current flaw detection probe 32 with preset values (allowable values of internal flaw and surface flaw, respectively) to judge propriety, and it drives a distribution mechanism 39 provided in the middle of the slider 38 serving as a valve conveyance path, described below, in order to guide a valve which is judged as improper (in the case where an inspection result of either one inspection is no good) to a slider dedicated for a waste valve (not shown).

Next, the operation of the valve transfer mechanism 40 by which valves 1 are transferred will be described in detail.

As illustrated in FIG. 2, the corresponding suction-pad jigs 45 support (suck and hold) a valve 1A held by the chuck 19 at the valve loading position P1, a valve 1B held by the first chuck 24 in the ultrasonic inspection chamber 20, and a valve 1C held by the second chuck 34 in the eddy-current inspection chamber 30 to ascend by a predetermined amount to advance (move to the right in FIG. 2) by a predetermined amount, and thereafter descend by a predetermined amount, so as to transfer the valves 1A, 1B, 1C which are supported (sucked and held) by the corresponding suction-pad jigs 45 respectively to the first chuck 24, the second chuck 34, and the valve unloading position P2, in substantially simultaneous, continuous, synchronous, and/or coordinated fashion.

In detail, in the ultrasonic inspection chamber 20, the suction-pad jig 45 releases supporting (sucking and holding) of the valve 1A at the same time of the first chuck 24 gripping and supporting the valve 1A supported (sucked and held) by the suction-pad jig 45, and in the eddy-current inspection chamber 30, the suction-pad jig 45 releases supporting (sucking and holding) of the valve 1B at the same time of the second chuck 34 gripping and supporting the valve 1B supported (sucked and held) by the suction-pad jig 45. Meanwhile, in the valve unloading position P2, the valve 1C released from supporting (sucking and holding) by the suction-pad jig 45 is made to slides along the slider 38 under its own weight.

Upon completion of transfer of the valves 1A, 1B, 1C, respectively, to the first chuck 24, the second chuck 34, and the valve unloading position P2, by the corresponding suction-pad jigs 45, the suction-pad jigs 45 ascend by a predetermined amount, retract by a predetermined amount together with the slide frame 42, and then descend by a predetermined amount, to return to the initial position.

Then, after the corresponding suction-pad jigs 45 transfer the valve 1A, 1B, 1C and until they retract to return to their initial positions, in the ultrasonic inspection chamber 20, the valve 1A transferred to the first chuck 24 is held by the first chuck 24 and made to descend by a predetermined amount so that it can be subjected to inspection of the stem joint 2a by the ultrasonic flaw detection probe 22 and thereafter ascend by the predetermined amount to return to the initial transfer position, and in the eddy-current inspection chamber 30, the valve 1B transferred to the second chuck 34 is held by the second chuck 34 and made to descend by the predetermined amount so that it can be subjected to inspection of the stem joint 2a by the eddy-current flaw detection probe 32 and thereafter ascend by the predetermined amount to return to the initial transfer position. During this period, the valve 1C transferred to the valve unloading position P2 is unloaded via the slider 38, while a new valve 1 to be inspected is loaded into the valve loading position P1 via the slider 18 serving as valve conveyance path.

Therefore, repeating three times the above series of the advancing and receding operations of the valve transfer mechanism 40 including the slide frame 42 and the three suction-pad jigs 45, i.e., the series of movements which comprises ascending, advancing descending, ascending, retracting, and descending in sequence, of each suction-pad jig 45, causes the valve 1 which was held at the valve loading position P1 to be transferred to the ultrasonic inspection chamber 20 so that it can be subjected to surface flaw inspection of the stem joint 2a, then, to be transferred to the eddy-current inspection chamber 30 so that it can be subjected to internal flaw inspection of the stem joint 2a and thereafter, to be transferred to the valve unloading position P2 to be unloaded.

As is obvious from the above description, according to this example, it is possible to inspect both the interior and surface of the stem joint 2a of the valve 1 by the single flaw inspection apparatus 10, so that flaw inspection equipment can be downsized and simplified.

Further, according to this example, transfer of a valve 1 from the valve loading position P1 to the ultrasonic inspection chamber 20, transfer of a valve 1 from the ultrasonic inspection chamber 20 to the eddy-current inspection chamber 30, and transfer of a valve 1 from the eddy-current inspection chamber 20 to the valve unloading position P2 are performed in substantially simultaneous, continuous, synchronous, and/or coordinated fashion; in particular, transfer of a valve 1 from a first flaw inspection apparatus and transfer of a valve to a second flaw inspection apparatus are performed as a substantially continuous series of operations of transfer of valves from the ultrasonic inspection chamber 20 to the eddy-current inspection chamber 30. Thus, cycle time required for internal and surface flaw inspection of a stem joint 2a of a valve 1 can be significantly shortened as compared with the situation in which these transfer operations are performed separately.

Moreover, according to this example, a valve 1 to which water adheres is not conveyed to the subsequent process via the slider 38 serving as the valve conveyance path. Thus, there is little or no possibility that the slider 38 will become wet, or that water adhering to the valve will interfere with processing during the subsequent process. Thus, this will make it unnecessary to provide water removing means such as a dryer or blower in the flaw inspection process.

In particular, this example is configured such that the three suction-pad jigs 45 can separately ascend and descend in the vertical direction with respect to the slide frame 42, the structure and control of driving of the valve transfer mechanism 40 become accordingly complicated. However, there are advantages as described below.

In other words, a valve 1 to be inspected may include valves having different specifications such as a different diameter of the valve head and a different entire length. Further, valve transfer positions in the valve transfer mechanism 40 including the predetermined valve loading position P1 and the predetermined valve unloading position P2 may be different in the vertical direction. However, since the suction-pad jigs 45 can separately ascend and descend in the vertical direction with respect to the slide frame 42, it is possible to accommodate the differences by adjusting the amount by which the suction-pad jigs 45 ascend and descend in the vertical direction in accordance with the specifications of the valve 1 or the height of the valve transfer positions, without any need to change the valve transfer positions.

Furthermore, this example is configured such that the suction-pad jigs 45 serving as the valve support can suspend and hold the valve 1 by sucking the valve face 4b. So, in order to carry out transfer of the valve 1 at a predetermined valve transfer position, it is sufficient that the suction-pad jig 45 ascends or descends so as to be directly above the valve transfer position. In other words, during transfer of the valve 1 by the suction-pad jigs 45 which ascend and descend, the suction-pad jigs 45 only come as close thereto as the predetermined positions above the slider 18 at the valve loading position P1, the first chuck 24 in the ultrasonic inspection chamber 20, the second chuck 34 in the eddy-current inspection chamber 30, and the slider 38 in the valve unloading position P2. Accordingly, there is no possibility of interference therewith by the suction-pad jigs 45. For this reason, in contrast to the case where the valve support in the valve transfer mechanism 40 is configured with, for example, a chuck jig which grips the stem 2 of the valve 1 instead of the suction-pad jig 45, there is no need to take some measures to prevent the valve support from interfering with the slider 18, the first chuck 24, the second chuck 34 or the slider 38 in this example.

Next, an apparatus 10A for flaw inspection of a stem joint of a valve according to a second example of the present invention will be described, with reference to FIG. 6.

The apparatus 10A for flaw inspection of the second example differs from the apparatus 10 for flaw inspection of the above described first example with respect to the following points.

First, the apparatus 10 for flaw inspection is such that the valve support of the valve transfer mechanism 40 configured by the suction-pad jig 45 which sucks the valve face 4a with negative pressure to support (suck and hold) the valve 1 with the stem 2 directed downward. And, the suction-pad jig 45 is configured in such a manner as to ascend and descend in the vertical direction with respect to slide frame 42 which is capable of advancing and receding in the horizontal direction.

On the other hand, the apparatus 10A for flaw inspection is configured such that the valve support of the valve transfer mechanism 40A configured with chuck jigs 45A each having a pair of claws 45b which open and close to clamp the stem 2. And, the chuck jigs 45A are fixed at lower ends of three arms 42a extending downward from a first slide frame 42A which advances/recedes in the horizontal direction and ascends/descends in the vertical direction, so as to be integrated with the first slide frame 42A.

Figure 6:
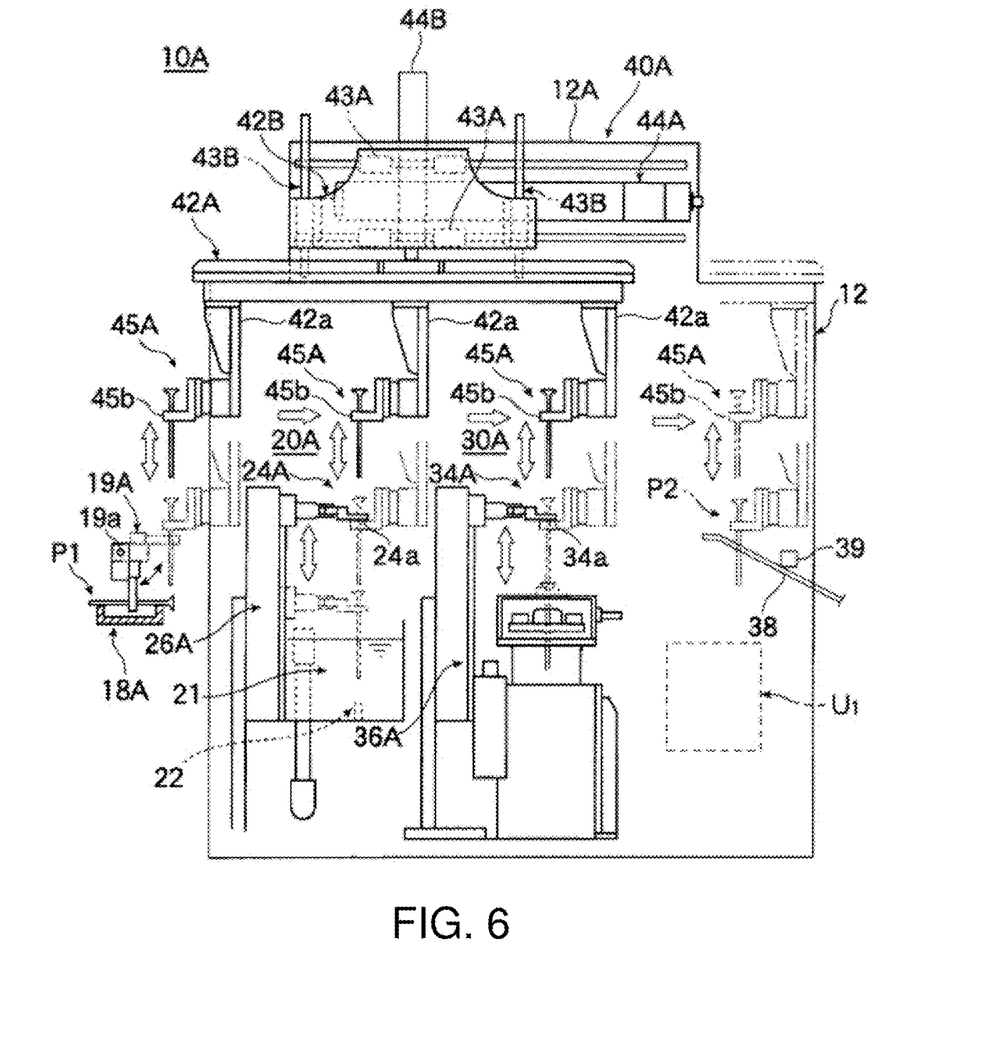
FIG. 6 is a front view of a flaw inspection apparatus according to a second example of the present invention.

In detail, as illustrated in FIG. 6, arranged above a housing 12 is a housing 12A which integrates with the housing 12 and extends in the horizontal direction. A second slide frame 42B having a separate body from the first slide frame 42A is configured in such a manner as to advance and recede in the horizontal direction with respect to the housing 12 (housing 12A) by a linear guide 43A extending in the horizontal direction and a drive mechanism 44A including a servo motor and a ball screw. The linear guide 43A and the drive mechanism 44A are interposed between the second slide frame 42B and the housing 12A. The first slide frame 42A can ascend and descend in the vertical direction with respect to the second slide frame 42B by a linear guide 43B extending in the vertical direction and a first-slide-frame drive mechanism 44B including a servo motor and a ball screw. The linear guide 43B and the drive mechanism 44B are interposed between the first slide frame 42A and the second slide frame 42B.

In other words, the valve transfer mechanism 40A includes the housing 12A integrated with the housing 12, the second slide frame 42B assembled to the housing 12A to be capable of advancing and receding in the horizontal direction, the first slide frame 42A assembled to the slide frame 42B to be capable of ascending/descending in the vertical direction, and the three chuck jigs 45A fixed and integrated with the first slide frame 42A.

Thus, the first slide frame 42A, which integrates the chuck jigs 45A is configured to advance/recede in the horizontal direction as well as ascend/descend in the vertical direction with respect to the housing 12.

For this reason, first, as it is no need to configure each chuck jig 45A to be slidable the vertical direction separately, the configuration of the valve transfer mechanism 40A is made simpler than that of the valve transfer mechanism 40 though the height of the entire housings 12 and 12A become greater.

Further, as each chuck jig 45A is not configured to be separately slidable in the vertical direction, the configuration of a control unit U1 which controls driving of the valve transfer mechanism 40A is simplified.

Secondly, in the first example, the first chuck 24 serving as the first valve holding mechanism in the ultrasonic inspection chamber 20 can ascend and descend in the vertical direction with respect to the housing 12 by the servo motor 25 and the drive mechanism 26 including the linear guide and ball screw interposed between the first chuck 24 and the housing 12, and the second chuck 34 serving as the second valve holding mechanism in the eddy-current inspection chamber 30 can ascend and descend in the vertical direction with respect to the housing 12 by the drive mechanism 36 including the linear guide and ball screw interposed between the second chuck 34 and the housing 12.

On the other hand, in this second example, a first chuck 24A serving as the first valve holding mechanism in the ultrasonic inspection chamber 20A can ascend and descend in the vertical direction with respect to the housing 12 by a drive mechanism 26A including a servo motor, a linear guide, and a ball screw. The drive mechanism 26A is interposed between the first chuck 24A and the housing 12. A second chuck 34A serving as the second valve holding mechanism in the eddy-current inspection chamber 30A can ascend and descend in the vertical direction with respect to the housing 12 by a drive mechanism 36A including a servo motor, linear guide, and a ball screw. The drive mechanism 36A is interposed between the second chuck 34A and the housing 12.

Thirdly, (the chuck jigs 45A of) the valve transfer mechanism 40A, the first chuck 24A in the ultrasonic inspection chamber 20A, and the second chuck 34A in the eddy-current inspection chamber 30A transfer the valve 1 therebetween. As the positions which the claws 24a of the first chuck 24A and the claws 34a of the second chuck 34A grip in the valve is closer to the valve head 4 than the position which the claws 45b of the chuck jig 45A grips, in the valve 1, opening and closing of the claws 45b of the chuck jigs 45A and the claws 24a, 34a of the first and second chucks 24A, 34A are controlled to avoid interference between the chuck jig 45A and the first chuck 24A and between the chuck jig 45A and the second chucks 34A, during transfer of the valves 1.

Specifically, when the valves 1 are transferred from the chuck jig 45A to the first chuck 24A and from the chuck jig 45A to the second chuck 34A, the claws 24a, 34a of the first and second chuck 24A, 34A open wide in synchronism with descent of the chuck jigs 45A so that the claws 45b of the chuck jig 45A can descend below the claws 24a, 34a. Then, at the same time that the claws 24a, 34a grip the stem 2 of the valve 1, the claws 45b of the chuck jigs 45A open wide to release the gripping of the stem 2 of the valve 1. Thus, the chuck jigs 45A can ascend without interfering with the first and second chucks 24A, 34A.

On the other hand, when the empty chuck jigs 45A receive a valve 1 from the first chuck 24A and the second chuck 34A, the claws 45b open wide in synchronism with descent of the chuck jigs 45A so as to descend below the claws 24a, 34a of the first and second chucks 24A, 34A gripping the valves 1. Then, at the same time of the claws 45b of the chuck jigs 45A grip the stems 2 of the valves 1, the claws 24a, 34a of the first and second chucks 24A, 34A open wide to release the gripping of the stems 2 of the valves 1. Thus, the chuck jigs 45A which have received the valves 1 can ascend without interfering with the first and second chucks 24A, 34A.

Fourthly, in the first example, a valve 1 is loaded to the valve loading position P1 with the slider 18 whereas, in this second example, the valve 1 is loaded to the valve loading position P1 by a V-shaped valve-loading guide 18A.

Further, provided at the valve loading position P1 is a chuck 19A capable of ascending/descending in the vertical direction and capable of swinging around a pivot 19a. The chuck 19A ascends by a predetermined amount while clamping (the stem 2 of) a valve 1 on the V-shaped guide 18A to swing around the pivot 19A (turn in the vertical direction) to hold the valve 1 in such fashion as to cause the face 4a to face upward so as to cause the face 4a to face chuck jig 45A of the valve transfer mechanism 40A.

As the constitution is in other respects similar to that of the apparatus 10 for flaw inspection of the first example, like elements have been given like reference numerals and duplicative description is omitted.

Figure 7:
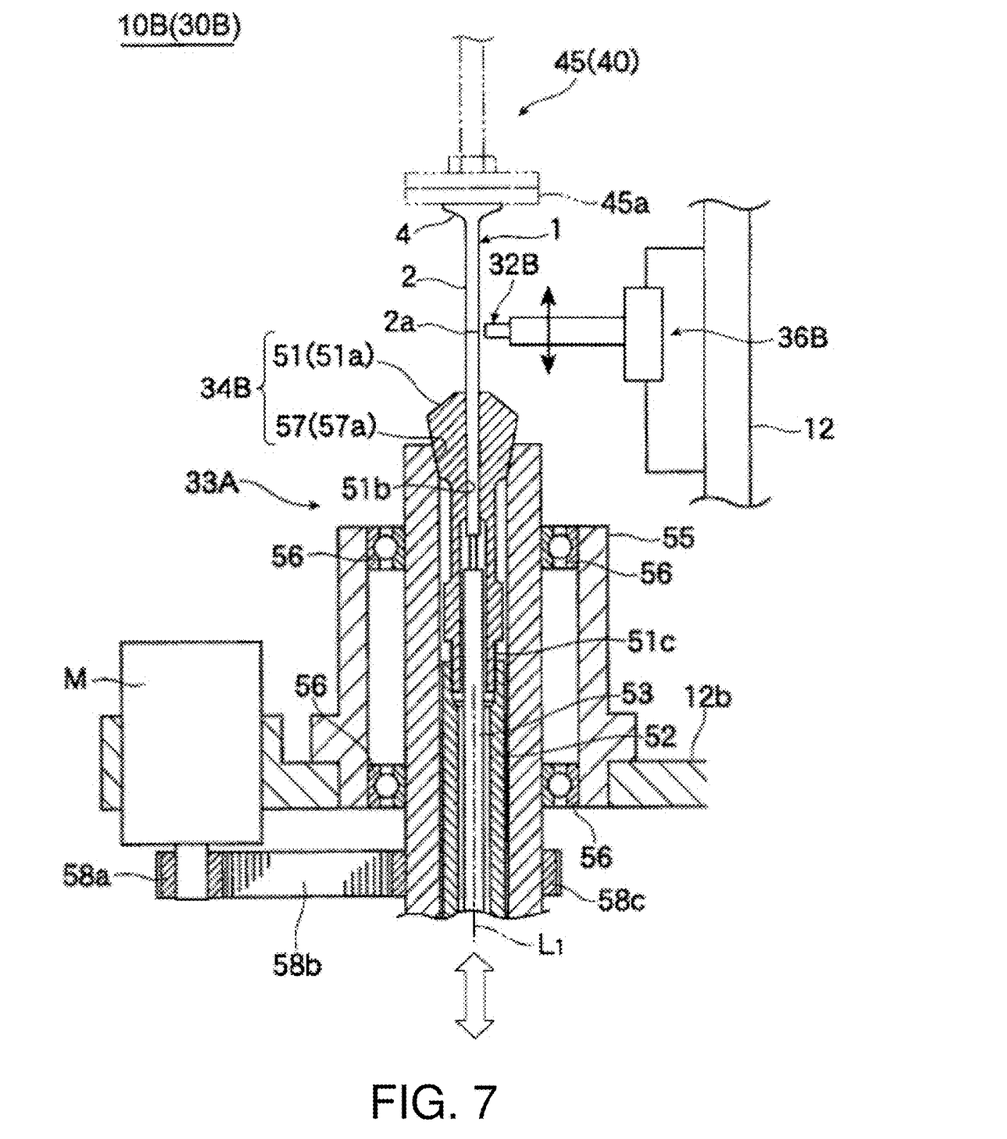
FIG. 7 is a longitudinal sectional view of an eddy-current inspection chamber in a flaw inspection apparatus according to a third example of the present invention.

Next, principal components in an apparatus 10B for flaw inspection according to a third example of the present invention will be described with reference to FIG. 7.

In both of the above first and second examples, as illustrated in FIGS. 5 and 6, in the eddy-current inspection chamber 30, 30A, a valve 1 transferred thereto from the ultrasonic inspection chamber 20, 20A by the valve transfer mechanism 40, 40A is made to descend while keeping the lower side face of the stem 2 including the stem joint 2a close to and facing the eddy-current flaw detection probe 32 which rotates integrally with the cylindrical body 31 so as to permit surface flaw inspection of the entire periphery of the stem joint 2a by the eddy-current flaw detection probe 32 while the stem 2 is supported by the second chuck 34, 34A.

In other words, the eddy-current flaw detection probe 32 rotates with respect to the valve 1 held by the second chuck 34, 34A in the eddy-current inspection chamber 30, 30A. In contrast, in the eddy current inspection chamber 30B of this third example, a valve 1 held by the second chuck 34B is made to rotate integrally with the second chuck 34B relative to the horizontally disposed eddy-current flaw detection probes 32B.

Specifically, in this third example, the second valve holding mechanism in the eddy-current inspection chamber 30B is constituted by a collet chuck 34B which grips the stem 2 with the face 4a facing upward.

That is, inside an outer cylinder 55 fixed to a base plate 12b, an inner cylinder 57 elongated in the vertical direction is rotatably supported via a bearing 56. An inner periphery surface of the upper end of the inner cylinder 57 is formed in a tapered shape to form a sleeve 57a, and a collet 51 having a head 51a with a tapered outer periphery surface matching with a tapered surface of the sleeve 57a is inserted into the inner cylinder 57. The collet 51 has a through hole 51b into which the stem 2 can be inserted. The head 51a of the collet 51 has three vertical slits (not shown) at equal intervals in the circumferential direction. Lower side 51c of the collet 51 is screwed by a cylindrical draw bar 52 capable of advancing and receding in the vertical direction by means of an air cylinder (not shown).

Enlarging/reducing the inner diameter of the head 51a of the collet 51 by the advancing/receding of the draw bar 52 in the axial direction enables the collet 51 to grip/release the stem 2 inserted into the through hole 51b of the collet 51. That is, the collet chuck 34B gripping the stem 2 of the valve 1 is constituted by the inner cylinder 57 having the sleeve 57a and the collet 51 which advances and recedes in the axial direction with respect to the inner cylinder 57. A positioning pin 53 extends into the draw bar 52 and collet 51 to adjust an amount by which the stem 2 is inserted into the collet chuck 34B.

Further, a servo motor M is disposed adjacent to the outer cylinder 55 in the base plate 12b. Rotation of the servo motor M is transmitted to the inner cylinder 57 via a driving pulley 58a, a belt 58b and a driven pulley 58c, so as to rotate the valve 1 integrally with the collet chuck 34B and inner cylinder 57. In other words, the rotation mechanism 33A which rotates the valve 1 around the rotation center axis L1 of the inner cylinder 57 is constituted by the inner cylinder 57 including the collet chuck 34B and rotatably supported by the collet chuck 34B, the servo motor M, the driving pulley 58a, the belt 58b and the driven pulley 58c.

Moreover, above the collet chuck 34B, the eddy-current flaw detection probe 32B is disposed at a predetermined position at which the eddy-current flaw detection probe 32B is made to be close to and facing the side face of the stem 2 including the stem joint 2a, gripped by the collet chuck 34B. The eddy-current flaw detection probe 32B can ascend and descend in the vertical direction along the stem 2 by a drive mechanism 36B including a servo motor, a linear guide, and a ball screw.

After the valve 1 is transferred to the collet chuck 34B by the suction-pad jig 45 of the valve transfer mechanism 40, the eddy-current flaw detection probe 32B may, for example, ascend with respect to the valve 1, which rotates integrally with the collet chuck 34B, while keeping close to and directly facing the side face of the stem 2 including the stem joint 2a, so as to perform a surface flaw inspection about the entire periphery of the valve joint 2a.

Description being similar in other respects to the descriptions given for corresponding components at apparatus 10 for flaw inspection in accordance with the first example, description that would be duplicative is omitted here.

As described above, methods and apparatuses for flaw inspection of stem joint(s) of engine valve(s) may employ ultrasonic flaw detection probe(s) and an eddy-current flaw detection probe(s) in a manner permitting downsizing of equipment and shortening of inspection cycle time.

Although the foregoing description as given in terms of the example of a valve in which a friction-weld joint or other such stem joint is employed to join a head member and a stem member of an engine valve, the present invention is not limited to engine valves but may be applied to friction-weld parts in general. Furthermore, the present invention is not limited to friction-weld joints or stem joints but may be applied to detection of flaws in general; for example, the present invention may be used to detect flaws at joints between metal parts regardless of the type of joint employed to join those parts.

While embodiments of the present invention have been described above, modes of carrying out the present invention are not limited to the foregoing embodiments, a great many further variations being possible without departing from the gist of the present invention. For any of the various function(s) described with reference to the attached drawings, so long as it would not interfere with ability to carry out the function(s) in question, the order of steps may be different from that described herein.

Although the terms vertical and horizontal were employed in the foregoing exemplary descriptions of preferred embodiments of the present invention, these directions were employed by way of example, there being no objection to application of the present invention to methods and apparatuses in which the corresponding directions are other than vertical and/or horizontal, e.g., direction(s) inclined relative to the vertical and/or the horizontal, and there furthermore being no objection to application of the present invention to pairs of directions that are not exactly mutually perpendicular, provided that there is at least an perpendicular component therebetween such that at least one effect of the present invention is at least partially achieved.

EXPLANATION OF REFERENCE NUMERALS

1 Poppet valve (engine valve)
2 Stem
2a Stem joint
2b Tip
4 Valve head
4a Face
10, 10A, 10B Apparatus for flaw inspection
12, 12A Housing
18, 38 Slider serving as valve conveyance path
20, 20A Ultrasonic inspection chamber
21 Tank
22 Ultrasonic flaw detection probe
24, 24A First chuck serving as first valve holding mechanism
24a Claw for clamping valve stem
25 Linear guide
26 Drive mechanism including linear guide and ball screw
26A, 36A, 36B Drive mechanism including servo motor, linear guide, and ball screw
30, 30A, 30B Eddy-current inspection chamber
32, 32B Eddy-current flaw detection probe
33, 33A Rotation mechanism
34, 34A Second chuck serving as second valve holding mechanism
34B Collet chuck serving as second valve holding mechanism
34a Claw for supporting valve head
35, 35A Servo motor
36, 36A Second-chuck drive mechanism 37 Aligning
40, 40A Valve transfer mechanism
42, 42A Slide frame
43 Linear guide
44 Drive mechanism including servo motor and ball screw
45 Suction-pad jig serving as valve support
45a Suction pad
45A Chuck jig serving as valve support
45b Claw of chuck jig
46, 46A Linear guide
47, 47A Drive mechanism including servo motor and ball screw
56 Bearing
P1 Valve loading position
P2 Valve unloading position
18, 38 Slider serving as valve conveyance path
19, 19A Chuck
U, U1 Control unit

What is claimed is:

1. A method for flaw inspection of an interior and a surface of a stem joint of an engine valve through use of an ultrasonic flaw detection probe and an eddy-current flaw detection probe, the method comprising:
an internal flaw inspection step comprising,
in an ultrasonic inspection chamber in a housing,
causing the ultrasonic flaw detection probe to be disposed so as to face upward in water in a tank,
holding the valve in such a way that a tip of a stem of the valve faces the ultrasonic flaw detection probe in the water, and
inspecting the interior of the stem joint with the ultrasonic flaw detection probe; and
a surface flaw inspection step comprising,
in an eddy-current inspection chamber adjacent to the ultrasonic inspection chamber in the housing,
causing the eddy-current flaw detection probe to be disposed horizontally,
holding the valve in such a way that a lower side face of a stem of the valve including the stem joint is close to and faces the eddy-current flaw detection probe, and
inspecting for a flaw on the surface of the stem joint with the eddy-current flaw detection probe while causing the eddy-current flaw detection probe to revolve about, and relative to, the outer periphery of the stem of the valve;
wherein a valve transfer mechanism capable of advancing and receding in a horizontal direction in which both inspection chambers are adjacent to each other integrally moves three valve supports positioned at intervals of a distance between the ultrasonic inspection chamber and the eddy-current inspection chamber, in the horizontal direction and vertical direction, so as to transfer the valve from a predetermined loading position to the ultrasonic inspection chamber, the valve which has completed internal flaw inspection in the ultrasonic inspection chamber to the eddy-current inspection chamber, and the valve which has completed surface flaw inspection in the eddy-current inspection chamber to a predetermined unloading position, in substantially synchronous fashion, while keeping the valve with the stem directed downward.

2. An apparatus for flaw inspection of an interior and a surface of a stem joint of an engine valve through use of an ultrasonic flaw detection probe and an eddy-current flaw detection probe, the apparatus comprising:
a housing;
an ultrasonic inspection chamber provided in the housing; and
an eddy-current inspection chamber provided in the housing adjacent to the ultrasonic inspection chamber in a horizontal direction,
the ultrasonic inspection chamber comprising
the ultrasonic flaw detection probe,
a tank in which the ultrasonic flaw detection probe is disposed so as to face upward in water, and
a first valve holding mechanism holding the valve at a predetermined position in which a tip of the stem of the valve faces the ultrasonic flaw detection probe,
the eddy-current inspection chamber comprising
the eddy-current flaw detection probe which is disposed horizontally,
a second valve holding mechanism holding the valve at a predetermined position in which a lower side face of a stem of the valve including the stem joint is close to and faces the eddy-current flaw detection probe, and
a rotation mechanism causing the eddy-current flaw detection probe to revolve about, and relative to, an outer periphery of the stem of the valve,
the housing comprising
a valve transfer mechanism having
three valve supports positioned at intervals of a distance between the first and the second valve holding mechanisms along the horizontal direction in which the ultrasonic inspection chamber and the eddy-current inspection chamber are adjacent and supporting the valve with the stem of the valve facing downward, the valve transfer mechanism transferring the valve from a predetermined loading position to the first valve holding mechanism, the valve which has completed internal flaw inspection and is held by the first valve holding mechanism to the second valve holding mechanism, and the valve which has completed surface flaw inspection and is held by the second valve holding mechanism to a predetermined unloading position, in substantially synchronous fashion, by virtue of the fact that the valve supports move integrally in the horizontal direction and a vertical direction, while keeping the valve with the stem directed downward; and
a control unit controlling drive of the valve transfer mechanism, the first and the second valve holding mechanisms, the ultrasonic flaw detection probe, the eddy-current flaw detection probe, and the rotation mechanism.

3. The apparatus for flaw inspection of a stem joint of an engine valve according to claim 2, wherein the valve transfer mechanism includes a slide frame capable of advancing and receding in a horizontal direction in which the ultrasonic inspection chamber and the eddy-current inspection chamber are adjacent to each other, and the valve supports mounted to be capable of ascending and descending with respect to the slide frame in a vertical direction.

4. The apparatus for flaw inspection of a stem joint of an engine valve according to claim 2, wherein the valve transfer mechanism includes a slide frame movable in a horizontal direction in which the ultrasonic inspection chamber and the eddy-current inspection chamber are adjacent to each other and capable of ascending and descending in a vertical direction, and the valve supports which are integrated with the slide frame.

5. An apparatus for flaw inspection of a stem joint of an engine valve, the apparatus comprising:
a housing;
an ultrasonic inspection chamber provided in the housing, the ultrasonic inspection chamber including
an ultrasonic flaw detection probe to inspect an interior of the stem joint of the engine valve, and
a tank in which the ultrasonic flaw detection probe is disposed so as to face upward in water;
an eddy-current inspection chamber provided in the housing adjacent to the ultrasonic inspection chamber, the eddy-current inspection chamber including
an eddy-current flaw detection probe which is disposed horizontally, the eddy-current flaw detection probe revolving about, and relative to, an outer periphery of the stem of the valve held in such a way that a lower side face of the stem of the valve including the stem joint is close to and faces the eddy-current flaw detection probe; and
a valve transfer mechanism having
three valve supports positioned at intervals of a distance between the ultrasonic inspection chamber and the eddy-current inspection chamber,
the valve transfer mechanism being capable of advancing and receding in a horizontal direction in which the ultrasonic inspection chamber and the eddy-current inspection chamber are adjacent, the valve transfer mechanism transferring the valve from a predetermined loading position to the ultrasonic inspection chamber, the valve which has completed internal flaw inspection to the eddy-current inspection chamber, and the valve which has completed surface flaw inspection to a predetermined unloading position, in substantially synchronous fashion, by virtue of the fact that the valve supports move integrally in the horizontal direction and a vertical direction, while keeping the valve with the stem directed downward.

* * * * *